US012765865B2

(12) United States Patent
Sheeran et al.

(10) Patent No.: US 12,765,865 B2
(45) Date of Patent: Oct. 20, 2026

(54) INTERFACE FOR TIME-BASED IMAGING PROTOCOLS

(71) Applicant: KONINKLIJKE PHILIPS N.V., Eindhoven (NL)

(72) Inventors: Paul Sheeran, Woodinville, WA (US); Liang Zhang, Issaquah, WA (US); Thanasis Loupas, Kirkland, WA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 175 days.

(21) Appl. No.: 18/686,158

(22) PCT Filed: Aug. 28, 2022

(86) PCT No.: PCT/EP2022/073865
§ 371 (c)(1),
(2) Date: Feb. 23, 2024

(87) PCT Pub. No.: WO2023/031070
PCT Pub. Date: Mar. 9, 2023

(65) Prior Publication Data

US 2024/0358353 A1 Oct. 31, 2024

Related U.S. Application Data

(60) Provisional application No. 63/238,247, filed on Aug. 30, 2021.

(51) Int. Cl.
*A61B 8/00* (2006.01)
*G06F 3/04847* (2022.01)
*G06F 3/0482* (2013.01)

(52) U.S. Cl.
CPC .............. *A61B 8/469* (2013.01); *A61B 8/465* (2013.01); *A61B 8/54* (2013.01); *G06F 3/04847* (2013.01); *A61B 8/481* (2013.01); *G06F 3/0482* (2013.01)

(58) Field of Classification Search
CPC .... G06F 3/048–05; A61B 8/465; A61B 8/481
See application file for complete search history.

(56) References Cited

U.S. PATENT DOCUMENTS

2002/0035326 A1* 3/2002 Kamiyama ......... G01S 7/52084 600/437
2003/0135116 A1* 7/2003 Ogasawara .............. A61B 8/00 600/437

(Continued)

FOREIGN PATENT DOCUMENTS

JP 2006197965 A 8/2006
JP 2011092748 A 5/2011

OTHER PUBLICATIONS

International Search Report and Written Opinion for PCT/EP2022/073865; Nov. 24, 2022, 8 pages.

(Continued)

*Primary Examiner* — Daniel Rodriguez

(57) ABSTRACT

A display (150) for a contrast-enhanced examination ultrasound (CEUS) exam is disclosed. The display (150) includes a user interface (160) with an editable protocol (200) adapted to allow a user to select time-based actions and events of an upcoming CEUS exam on the display (150); a first time-bar display (300) adapted to allow the user to alter time-based actions during the CEUS exam, and to provide visual indications of upcoming actions on the display (150); and a second time-bar display (400) adapted to allow the user to display (150) images (512) and loops acquired during the CEUS exam on the display (150). A method (600) of controlling an imaging procedure is also described.

26 Claims, 6 Drawing Sheets

(56) References Cited

U.S. PATENT DOCUMENTS

| | | | | |
|---|---|---|---|---|
| 2004/0133107 | A1* | 7/2004 | Hashimoto | A61B 8/481 600/437 |
| 2004/0254465 | A1* | 12/2004 | Sano | A61B 8/12 600/443 |
| 2008/0119715 | A1* | 5/2008 | Gonzalez Molezzi | A61B 5/7285 600/407 |
| 2009/0012821 | A1* | 1/2009 | Besson | H04N 21/4347 715/740 |
| 2011/0054266 | A1* | 3/2011 | Dinino | G01S 7/52074 600/300 |
| 2014/0125691 | A1* | 5/2014 | Lysyansky | A61B 8/0883 345/672 |
| 2014/0143710 | A1* | 5/2014 | Zhao | G16H 30/40 715/835 |
| 2014/0187946 | A1* | 7/2014 | Miller | A61B 8/4245 600/443 |
| 2015/0190111 | A1* | 7/2015 | Fry | A61B 5/022 600/438 |
| 2015/0289840 | A1* | 10/2015 | Konofagou | A61B 8/485 600/438 |
| 2016/0354060 | A1* | 12/2016 | Perrey | A61B 8/465 |
| 2017/0090694 | A1* | 3/2017 | Lee | G06F 3/0485 |
| 2017/0156698 | A1* | 6/2017 | Park | A61B 8/463 |
| 2017/0163869 | A1* | 6/2017 | Semba | A61B 6/465 |
| 2018/0092629 | A1* | 4/2018 | Yoneyama | A61B 8/06 |
| 2018/0220993 | A1* | 8/2018 | Poland | A61B 8/56 |
| 2018/0253842 | A1* | 9/2018 | Allmendinger | G06N 20/00 |
| 2019/0076127 | A1* | 3/2019 | Aase | A61B 5/329 |
| 2020/0155121 | A1* | 5/2020 | Kwon | A61B 8/06 |
| 2020/0330073 | A1* | 10/2020 | McLaughlin | A61B 8/4405 |
| 2021/0015463 | A1* | 1/2021 | Shiran | A61B 8/0883 |
| 2021/0059631 | A1* | 3/2021 | Lewis | A61B 6/465 |
| 2021/0216356 | A1* | 7/2021 | Arnaudov | G06F 9/46 |
| 2022/0061812 | A1* | 3/2022 | Morrise | A61B 8/465 |
| 2022/0202384 | A1* | 6/2022 | Saiki | G06F 3/0486 |
| 2022/0291823 | A1* | 9/2022 | Siddanahalli Ninge Gowda | G06V 20/46 |
| 2023/0054209 | A1* | 2/2023 | Roh | A61B 34/76 |

OTHER PUBLICATIONS

"SonixTouch Ultrasound System User Manual," retrieved from http://www.ultrasonix.com, 396 pages.

* cited by examiner

INTERFACE FOR TIME-BASED IMAGING PROTOCOLS

CROSS-REFERENCE TO PRIOR APPLICATIONS

This application is the U.S. National Phase application under 35 U.S.C. § 371 of International Application No. PCT/EP2022/073865, filed on Aug. 28, 2022, which claims the benefit of U.S. Provisional Patent Application No. 63/238,247, filed on Aug. 30, 2021. These applications are hereby incorporated by reference herein.

BACKGROUND

Contrast-enhanced imaging, such as contrast enhanced ultrasound (CEUS) imaging requires multiple steps to be executed in a specific sequence, which is often referred to as a protocol. Known CEUS imaging protocols require timely action by an operator and are done manually. For example, once entering a contrast mode, the operator is required to initiate a contrast injection, and begin timing the procedure upon arrival of first bubbles in the contrast medium. Shortly before or after the incidence of the first bubbles, the operator must begin acquiring images or imaging loops over time, or both.

After initial acquisition of images and/or loops, the operator typically terminates image/loop acquisition after a designated period of time (e.g., 30-60 s). Often, this image/loop acquisition initiation and termination sequence may be repeated at predetermined time intervals to capture images/loops at desired times of the contrast agent circulation. For example, the acquisition of images/loops may be repeated to capture a 10 s imaging loop every 30 s, or to capture 10 images 10 s apart.

During an imaging sequence of a subject, it is sometimes desired to freeze the ultrasound transducer so that ultrasonic waves are not transmitted for a certain period of time to reduce the incidence of contrast bubble destruction. This is done a number of times during an imaging procedure of the subject between image/loop capture sequences.

Moreover, there are times when another injection of contrast agent is useful during an imaging procedure. Often, the repeated injection is initiated after a predetermined duration of time.

Known imaging protocols, such as those described above, are carried out manually, with the operator of the imaging system beginning and terminating various steps by manual timing. These imaging protocols often entail a comparatively difficult workflow, which requires precision in both imaging and contrast injection timing. As will be appreciated, known methods that require manual execution of timed sequences of image acquisition and manipulation required in some imaging modes, such as contrast-enhanced ultrasound imaging, is challenging and fraught with errors in image acquisition initiation and termination, resulting in loss of data and/or the need for repeated injections.

What are needed, therefore, are a device, method and system that overcomes at least the drawbacks of known methods and systems described above.

SUMMARY

According to an aspect of the present disclosure, a display for a contrast-enhanced examination ultrasound (CEUS) exam is disclosed. The display comprises: a menu comprising an editable protocol adapted to allow a user to select time-based actions and events of an upcoming CEUS exam on the display: a first time-bar display adapted to allow the user to alter time-based actions during the CEUS exam, and to provide visual indications of upcoming actions on the display; and a second time-bar display adapted to allow the user to display images and loops acquired during the CEUS exam on the display.

According to another aspect of the present disclosure, a method of controlling an imaging procedure is disclosed. The method comprises: providing a menu comprising editable protocol adapted to allow a user to select time-based actions and events of an upcoming contrast enhanced ultrasound (CEUS) exam on a display: providing a first time-bar display adapted to alter time-based actions during the CEUS exam, and provide visual indications of upcoming actions on the display; and providing a second time-bar display configured to display images and loops acquired during the CEUS exam on the display.

According to another aspect of the present disclosure, a tangible, non-transitory computer-readable medium that stores instructions is disclosed. The instructions, when executed by a processor, cause the processor to: provide a menu comprising editable protocol adapted to allow a user to select time-based actions and events of an upcoming contrast enhanced ultrasound (CEUS) exam on a display: provide a first time-bar display adapted to alter time-based actions during the CEUS exam, and provide visual indications of upcoming actions on the display; and provide a second time-bar display configured to display images and loops acquired during the CEUS exam on the display.

BRIEF DESCRIPTION OF THE DRAWINGS

The representative embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

In the following detailed description, for the purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted so as to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing particular embodiments only and is not intended to be limiting. The defined terms are in addition to the technical and scientific meanings of the defined terms as commonly understood and accepted in the technical field of the present teachings.

It will be understood that, although the terms first, second, third, etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing particular embodiments only and is not intended to be limiting. As used in the specification and appended claims, the singular forms of terms "a." "an" and "the" are intended to include both singular and plural forms, unless the context clearly dictates otherwise. Additionally, the terms "comprises." "comprising." and/or similar terms specify the presence of stated features, elements, and/or components, but do not preclude the presence or addition of one or more other features, elements, components, and/or groups thereof. As used herein, the term "and/or" includes any and all combinations of one or more of the associated listed items.

By the present teachings, implementation of an imaging protocol is facilitated using a menu on a display, a user interface and/or a GUI, real time reminders and alerts provided on a display, and image/loop review on the display. Notably, the real time reminders and alerts may also be audible. Among other benefits, better control of an imaging procedure, fewer errors during the imaging procedure, and facilitated review of images/loops acquired during the imaging procedure are realized.

Figure 1:
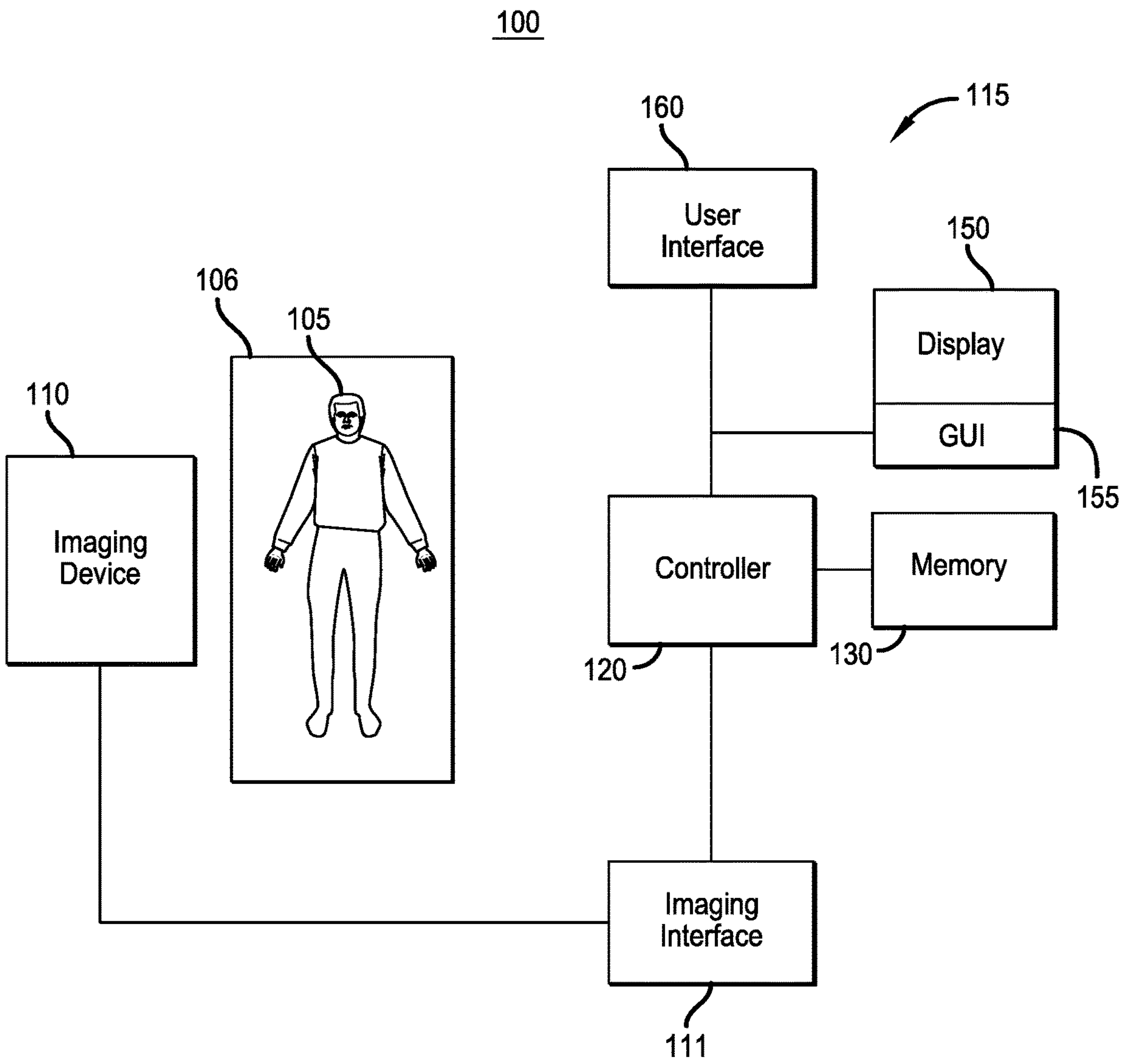
FIG. 1 is a simplified block diagram of a system for imaging a portion of a body, according to a representative embodiment.

FIG. 1 is a simplified block diagram of an imaging system 100 for imaging a region of interest of a subject, according to a representative embodiment.

Referring to FIG. 1, the imaging system 100 comprises an imaging device 110 and a computer system 115 for controlling imaging of a region of interest in a patient 105 on a table 106. The imaging device 110 is illustratively an ultrasound imaging system capable of providing an US image scan of a region of interest in the patient 105. Illustratively, the imaging device 110 is of the type commonly used in CEUS imaging procedures, and is adapted to provide color Doppler imaging or three dimensional flow volumetry imaging. CEUS imaging procedures typically involve the combining of a contrast imaging mode and a standard B-mode. In some cases, contrast is combined with flow modes (including color Doppler, but also power Doppler or other approaches). Contrast is also combined with needle visualization modes for biopsy/ablation procedures, and contrast can also be executed in modes that co-register CEUS images with pre-existing datasets from other modalities (e.g., Computer Tomography (CT), Magnetic Resonance Imaging (MR) and a previous ultrasound (US) exam). Notably, any of these various imaging methods may be in two dimensions (2D) or three dimensions (3D).

The computer system 115 receives image data from the imaging device 110, and stores and processes the imaging data according to representative embodiments described herein. The computer system 115 comprise a controller 120, a memory 130, a display 150 comprising a graphical user interface (GUI) 155, and a user interface 160. The display 150 may also include a loudspeaker (not shown) to provide audible feedback.

The controller 120 interfaces with the imaging device 110 through an imaging interface 111. The memory 130 stores instructions executable by the controller 120. When executed, and as described more fully below, the instructions cause the controller 120 to allow the user to schedule different steps of a protocol using the GUI 155 or the user interface 160, or both, and to selectively retrieve images or loops, or both taken at certain times during the exam (e.g., CEUS exam). In addition, the controller 120 may implement additional operations based on executing instructions, such as instructing or otherwise communicating with another element of the computer system 115, including the memory 140 and the display 150, to perform one or more of the above-noted processes.

The controller 120 is representative of one or more processing devices, and is configured to execute software instructions stored in memory 130 to perform functions as described in the various embodiments herein. The controller 120 may be implemented by field programmable gate arrays (FPGAs), application specific integrated circuits (ASICs), a general purpose computer, a central processing unit, a computer processor, a microprocessor, a graphics processing unit (GPU), a microcontroller, a state machine, programmable logic device, or combinations thereof, using any combination of hardware, software, firmware, hard-wired logic circuits, or combinations thereof. Additionally, any processing unit or processor herein may include multiple processors, parallel processors, or both. Multiple processors may be included in, or coupled to, a single device or multiple devices.

The term "processor" as used herein encompasses an electronic component able to execute a program or machine executable instruction. References to a computing device comprising "a processor" should be interpreted to include more than one processor or processing core, as in a multi-core processor. A processor may also refer to a collection of processors within a single computer system or distributed among multiple computer systems, such as in a cloud-based or other multi-site application. The term computing device should also be interpreted to include a collection or network of computing devices each including a processor or processors. Programs have software instructions performed by one or multiple processors that may be within the same computing device or which may be distributed across multiple computing devices.

The memory 130 may include a main memory and/or a static memory, where such memories may communicate with each other and the controller 120 via one or more buses. The memory 130 stores instructions used to implement some or all aspects of methods and processes described herein. The memory 130 may be implemented by any number, type and combination of random access memory (RAM) and read-only memory (ROM), for example, and may store various types of information, such as software algorithms, which serves as instructions, which when executed by a processor cause the processor to perform various steps and methods according to the present teachings. Furthermore, updates to the methods and processes described herein may also be provided to the computer system 115 and stored in memory 130.

The various types of ROM and RAM may include any number, type and combination of computer readable storage media, such as a disk drive, flash memory, an electrically programmable read-only memory (EPROM), an electrically erasable and programmable read only memory (EEPROM), registers, a hard disk, a removable disk, tape, compact disk read only memory (CD-ROM), digital versatile disk (DVD), floppy disk, Blu-ray disk, a universal serial bus (USB) drive, or any other form of storage medium known in the art. The memory 130 is a tangible storage medium for storing data and executable software instructions, and is non-transitory during the time software instructions are stored therein. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. The memory 130 may store software instructions and/or computer readable code that enable performance of various functions. The memory 130 may be secure and/or encrypted, or unsecure and/or unencrypted.

"Memory" is an example of computer-readable storage media, and should be interpreted as possibly being multiple memories or databases. The memory or database may for instance be multiple memories or databases local to the computer, and/or distributed amongst multiple computer systems or computing devices. A computer readable storage medium is defined to be any medium that constitutes patentable subject matter under 35 U.S.C. § 101 and excludes any medium that does not constitute patentable subject matter under 35 U.S.C. § 101. Examples of such media include non-transitory media such as computer memory devices that store information in a format that is readable by a computer or data processing system. More specific examples of non-transitory media include computer disks and non-volatile memories.

The user interface 160 may include a user and/or network interface for providing information and data output by the controller 120 and/or the memory 130 to the user and/or for receiving information and data input by the user. That is, the user interface 160 enables the user to enter data and to schedule, control or manipulate aspects of the processes described herein, and enables the controller 120 to indicate the effects of the user's control or manipulation. The user interface 160 may include one or more of ports, disk drives, wireless antennas, or other types of receiver circuitry. The user interface 160 may further connect one or more user interfaces, such as a mouse, a keyboard, a mouse, a trackball, a joystick, a microphone, a video camera, a touchpad, a touchscreen, voice or gesture recognition captured by a microphone or video camera, for example.

The display 150 may be a monitor such as a computer monitor, a television, a liquid crystal display (LCD), a light emitting diode (LED) display, a flat panel display, a solid-state display, or a cathode ray tube (CRT) display, or an electronic whiteboard, for example. The display 150 may also provide a graphical user interface (GUI) 155 for displaying and receiving information to and from the user.

As alluded to above, and as described in more detail below, in accordance with various representative embodiments, various aspects of imaging protocols may be selectively scheduled by the user to carry out certain desired functions during an imaging procedure. Moreover, in accordance with representative embodiments, reminders may be provided to the user during the execution of the imaging protocol. Furthermore, after the imaging scan is completed, in accordance with representative embodiments, review of acquired images/loops is facilitated by pairing of the images/loops to a particular time of the executed protocol. For purposes of illustration, and not limitation, FIGS. 2-6 and their descriptions present various aspects of a CEUS protocol execution by the present teachings. It is emphasized that this is merely an illustrative application of the various aspects of the present teachings, and is not intended to limit the scope of the present teachings.

Figure 2:
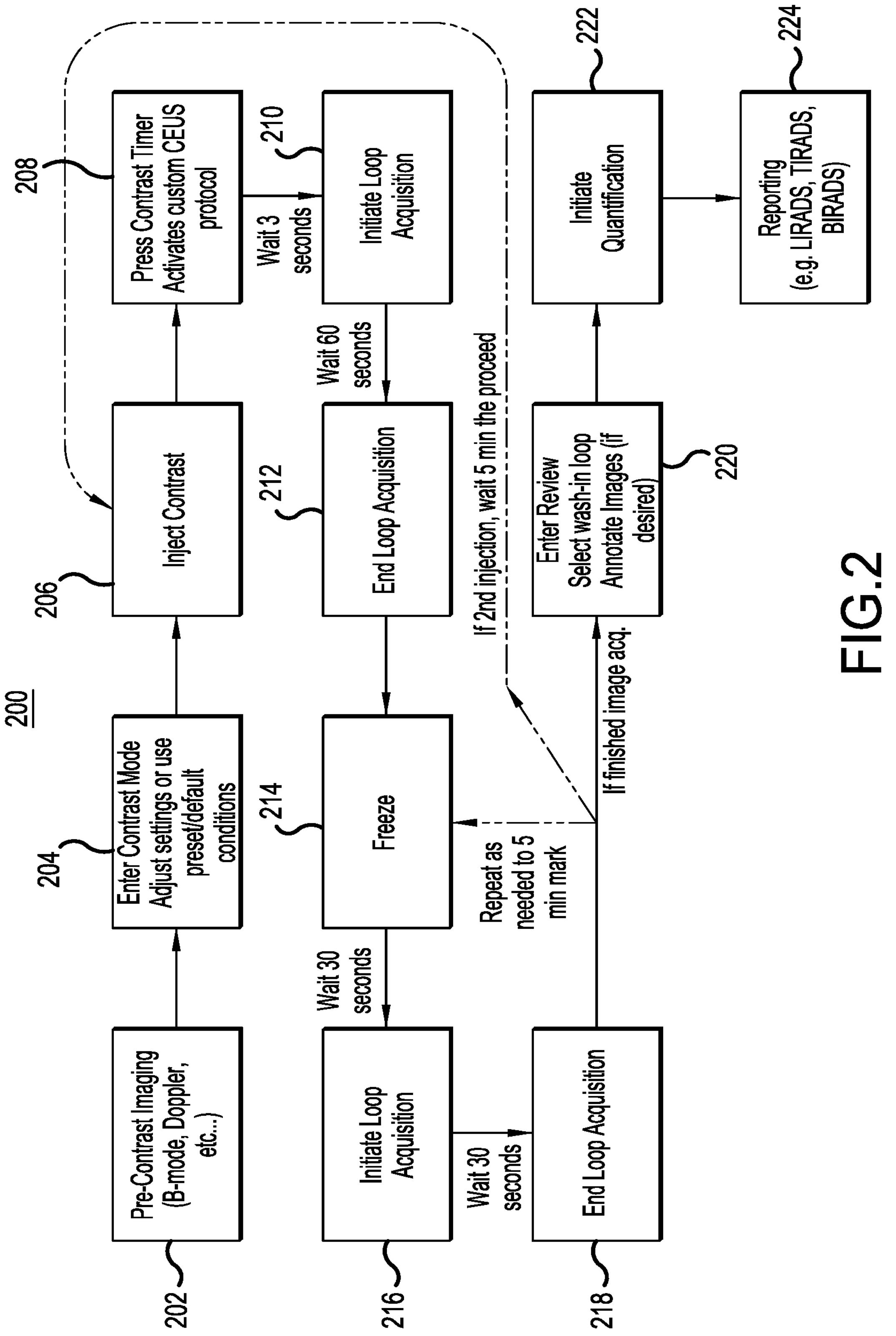
FIG. 2 is a simplified flow diagram of a CEUS protocol, according to a representative embodiment.

FIG. 2 is a simplified flow diagram showing a protocol 200 for imaging blood flow, according to a representative embodiment. Various aspects and details of the protocol 200, and its implementation are contemplated for use in the imaging system 100 described above. Various aspects of the imaging system 100 may not be repeated in order to avoid obscuring the discussion of the present representative embodiment.

The protocol 200 is illustratively a CEUS protocol and includes common steps and actions used in CEUS imaging. Again, it is emphasized the application of the present teachings to CEUS imaging is merely illustrative, and the various aspects of the present teachings are contemplated for use in other imaging modalities. Furthermore, various aspects and details of the protocol 200 and the attendant method are common to those described above, and may not be repeated in order to avoid obscuring the discussion of the present representative embodiment.

As alluded to above, and as described more fully below, various steps in the sequence of the protocol are implemented using a menu (not shown in FIGS. 1 and 2) on the display 150, and the user interface 160 or the GUI 155, or both. Moreover, instructions stored in the memory 130, which when executed by a processor of the controller 120, enable the selection of various desired steps in the protocol 200, and, during and after imaging, enable the selection of images and loops by the user through the user interface 160, or the GUI 155, or both.

The protocol 200 begins at 202 with a pre-contrast imaging step performed by the user/operator of the imaging system 100 on which the protocol 200 is carried out. Like all other steps in the protocol, the pre-contrast imaging step may be selected using a menu (not shown in FIGS. 1 and 2) on the display 150 using the user interface 160, or the GUI 155, or both.

After completion of the pre-contrast imaging step at 202, the protocol 200 continues with entry of a contrast mode at 204 in which various settings are adjusted, or in which preset default conditions are selected. Entrance in the contrast mode at 204 is done during the scheduling sequence of the protocol 200, and may be selected using a menu (not shown in FIGS. 1 and 2) on the display 150 using the user interface 160, or GUI 155, or both.

The protocol 200 continues with injection of a contrast agent at 206 into the subject or patient. The injection of the contrast agent at 206 is scheduled during the scheduling sequence of the protocol 200. The injection of the contrast agent at 206 using the user interface 160 of the GUI 155 to select the injection of the contrast agent from a menu (not shown in FIGS. 1 and 2) on the user interface 160, or GUI 155, or both. As will be appreciated by one of ordinary skill in the art, the injection of the contrast agent and the subsequent appearance of the contrast agent in the arterial or portal or venous circulation triggers certain timers that are used to carry out the protocol at certain times. Notably, as described more fully below these timers can also be set during the scheduling sequence of the protocol. Moreover, and as described more fully below, alerts denoting the specified time when an operator must take action can be displayed on the display 150 during an imaging scan, or can be provided by audio or haptic feedback from the display 150, or a by selection of a combination of these options during the scheduling of the protocol 200.

After completion of injection of the contrast agent at 206, the user may select to activate a contrast timer at 208 using the user interface 160, or the GUI 155 to select the time and duration of the timer from a menu (not shown in FIGS. 1 and 2). The activation of the contrast timer at 208 causes a custom CEUS protocol to begin. As described more fully below, the various actions and timers used in the custom CEUS protocol may be selected on the display 150 using the user interface 160, or the GUI 155, or both.

After activation of the contrast timer at 208, imaging and loop acquisition be carried out after injection of the contrast agent to ensure first arrival of the contrast agent, and subsequently the early arterial phases. Notably, as described more fully below, the commencement and termination of this contrast timer at 208 may be displayed on the screen, or an alert to signal its termination may be provided by the display 150, or both. In this manner, the user or operator of the imaging system 100 is able to initiate an image acquisition loop at 210. Alternatively, prior to commencement of the protocol 200, the user may set a user timer using a menu (not shown in FIGS. 1 and 2) on the display 150 with the user interface 160 or GUI 155. As such, the user timer of this waiting period after injection of the contrast agent at 208 may be set and activated during the configuring of the protocol 200 by the user/operator. Illustratively, the user timer of the waiting period can be selected by the user/operator using the user interface 160, and/or the GUI 155 to select the time and duration of the timer from a menu (not shown in FIGS. 1 and 2). Further descriptions of the selection of timers and their alerts are provided below in accordance with various representative embodiments. Notably, and as described more fully below, the user can designate functions such as initiating acquisition if images/loops, freezing, etc., based on the user timer sequence and definitions in the protocol.

The duration of the image acquisition loop beginning at 210 is beneficially selectable by the present teachings, as are the acquisition frame rates. The duration of the image acquisition loop beginning at 210 may be selected by the user/operator using the user interface 160 and/or the GUI 155 via a selection on the menu (not shown in FIGS. 1 and 2). Notably, contrast examinations often have high variability across patients, injections, and lesion types. At a basic level, the contrast examination aims to sample wash-in, which is the increase in pixel intensity over the initial time period that occurs as a result of the contrast agent's arriving in the imaging plane due to transit in the circulatory system during an arterial phase through the peak contrast arrival (frames at which the maximum signal power or pixel intensity occurs in the organ of interest). In this part of the imaging sequence, high frame rates are useful to sample the rapid changes. After this, there is a gradual decay of the agent to sample wash-in, which is the increase in pixel intensity over the initial time period that occurs as a result of the contrast agent arriving in the imaging plane due to transit in the circulatory system. After the arterial phase has been sampled, and the user is capturing portal/late phase performance, the demands on frame rate are relaxed, and tradeoffs can be made to maximally preserve contrast agent and reduce data size (e.g. by reducing number of transmits per second). Accordingly, and as will be appreciated by one of ordinary skill in the art, the selected duration of the image acquisition loop at 210 of the protocol 200 beneficially allows improved imaging efficiency and accuracy to be carried out by the user/operator.

Next, after the duration of the loop acquisition at 210, the loop acquisition is terminated at 212. The duration of the loop acquisition at 210 may be displayed on the screen, or an alert to signal the termination of the duration of the loop acquisition at 210, or both, may be provided by the display 150. In this manner, the user or operator of the imaging system 100 is able to terminate an image acquisition loop at 212. Alternatively, the user may set the timer using a menu (not shown in FIGS. 1 and 2) on the user interface 160 or GUI 155 prior to commencement of the protocol 200 to terminate the acquisition of a loop that began at 210, and is terminated at 212. As such, the timer of this waiting period after injection of the contrast agent at 208 may be set and activated during the configuring of the protocol 200 by the user/operator.

The length of the arterial phase may vary significantly based on organ, patient health, and other factors. The length of time from peak contrast signal to late-phase can also vary significantly based on organ, patient, and lesion. For example, in some patients the contrast agent may clear quickly and cease to provide any useful signal past 1 or 2 minutes. In these cases, the protocol 200 may be usefully configured to enable the user/operator to bypass multiple upcoming events to advance to the review/quantification/reporting stages. Similarly, the ideal time to make changes to acoustic properties (e.g. acquisition frame rate, transmit line density, etc.) in order to preserve contrast agent may not be consistent from patient to patient, but rather may depend on where in the wash-in/wash-out sequence the user is currently. Finally, and as discussed more fully below, annotation and marking of loops/frames of interest have benefits to quantification and reporting that happen post-exam. These annotations and markings may be carried out via the user interface 160 or the GUI 155, or both.

After termination of the loop acquisition at 212, the imaging system 100 may enter a freeze mode at 214. The freezing of the imaging system halts transmission of ultrasound waves to the body. This may be done for a number of reasons, including, for example, to preserve bubbles in the contrast agent, which may be diminished or eliminated by the ultrasonic waves. The freezing at 214 is generally effected when the images that can be gathered are not of interest, or are not useful to the particular scan being undertaken. In certain imaging procedures, the contrast agent level reaches a peak level and subsequently the level decays over time or reaches a steady state. During these times, it may be not be useful to gather images. Moreover, there are a number of factors that drive the duration of the freeze, including, but not limited to the behavior of a certain type of lesion with respect to the contrast agent. Accordingly, the initiation and duration of the freeze at 214 may vary depending on various factors. As such, the selection of the commencement and termination of the freeze at 214 is beneficially controllable. Notably, the freezing and unfreezing may be done based on image observation by the operator, or may be fixed by the protocol. Specifically, in some organizational situations, the radiologist would set a strict protocol that all technologists must follow. This would result in a fixed duration so that all presented similarly to the radiologist. In other circumstances, the radiologist/doctor may carry out the scan, and may alter timing based on observations. In yet other circumstances, the data collection may be part of clinical research, where adherence to strict protocols requiring fixed duration is beneficial.

Commencement and termination (i.e., duration) of the freezing of the imaging system 100 at 214 may be displayed on the display, or an alert to signal its termination may be provided by the display 150, or both. In this manner, the user or operator of the imaging system 100 is able to initiate and terminate freezing of the imaging system 100 at 214 for a desired period of time by interaction with the display 150 in real time using a menu (not shown in FIGS. 1 and 2) on the user interface 160 or GUI 155. Alternatively, the user may set the timer using the user interface 160 or GUI 155 prior to commencement of the protocol 200. As such, the timer of this freeze of data gathering at 214 may be set and activated during the configuring of the protocol 200 by the user/operator.

After termination of the freeze at 214, another loop acquisition is initiated at 216. In this manner. In either case, the user or operator of the imaging system 100 is able to initiate another image acquisition loop at 216. Again, the time to commence the next loop acquisition at 216 may be shown on the display 150, or an alert to signal its termination may be provided by the display 150, or both. Alternatively, the user may set the timer using a menu (not shown in FIGS. 1 and 2) on the user interface 160 or GUI 155 prior to commencement of the protocol 200. As such, the timer of this freeze period may be set and activated during the configuring of the protocol 200 by the user/operator.

Next, after the duration of the loop acquisition at 216, the loop acquisition is terminated at 218. The duration of the loop acquisition (illustratively 30 s) may be shown on the display, or an alert to signal the termination of the duration may be provided by the display 150, or both. In this manner, the user or operator of the imaging system 100 is able to terminate an image acquisition loop at 218. Alternatively, the user may set the timer using the user interface 160 or GUI 155 prior to commencement of the protocol 200 to terminate the acquisition of a loop that began at 216, and is terminated at 218. As such, the timer of the image acquisition at 218 may be set and activated during the configuring of the protocol 200 by the user/operator.

After termination of the acquisition of the loop that began at 216, the protocol 200 continues to the next stage of the imaging sequence. Notably, at 220 the user/operator may advance to the review of the acquired images/loops, select a wash-in loop, or annotate the images gathered during the scans. As described more fully below, the user/operator may perform thesc functions on the display 150 using the user interface 160 or the GUI 155, or both.

After completing the review and other actions at 220, the protocol proceeds to initiate quantification at 222. The quantification at 222 generally comprises the launching of internal or external applications that analyze the key CEUS images/loops for quantification parameters of interest. For example, it may be useful to study how the time versus intensity properties differ between pixels in healthy tissue and pixels in a lesion of interest. These analyses are used as additional inputs to diagnosis or reporting. Illustratively, the user can initiates quantification by manipulating the GUI while in review or freeze and selecting from a GUI button that launches the quantification toolset with the current loop as input.

Finally, upon completion of the quantification at 222, the protocol 200 proceeds to 224 to report the various findings according to a desired reporting protocol such as ultrasound liver Imaging reporting and data system (LIRADS): thyroid imaging, reporting and data system (TIRADS): or breast imaging and reporting data system (BIRADS) to mention only a few. The reporting protocol selected can be set prior to the beginning of the protocol 200 using a menu (not shown in FIGS. 1 and 2) on the display 150, and the user interface 160 or the GUI 155, or both. Moreover, the reporting could be customized by the user. For example, the user could use the protocols to select a customized version of the TIRADS report based on differences in Asia, if desired. Rather than proceeding to review images at 220, it may be desired to repeat the freeze at 214, followed by proceeding to loop acquisition at 216 and the loop acquisition is terminated at 218. For example, if the contrast has not washed out and there is motivation to continue sampling the properties of the agent (for example, the lesion exhibits unusual decay properties or the clinician is uncertain about the classification without further observation), one may want to extend the exam in increments of the loop in 214-218. Repeating the sequence beginning with the freeze at 214 can be done in real time using a menu (not shown in FIGS. 1 and 2) on the display 150, and the user interface 160 or the GUI 155, or both. Notably, a delay prior to repeating the sequence may be added by the user/operator using the display 150, and the user interface 160 or the GUI 155, or both. Alternatively, the delay can be set a priori. For example, a default protocol could choose to repeat this sequence until the total elapsed time since injection is on the order of 3 min to 5 min, which are typical of CEUS washout timeframes.

Alternatively, the user/operator may decide to introduce a second injection of contrast agent as shown. This may be done for one of a number of reasons, such as when the operator believes the first set of images/loops are not suitable for analysis. Alternatively, if the user/operator has found additional lesions in the course of a first exam, additional imaging may be carried out to further investigate. Repeating the sequence beginning with the at 206 can be done in real time using a menu (not shown in FIGS. 1 and 2) on the display 150, and the user interface 160 or the GUI 155, or both.

Figure 3:
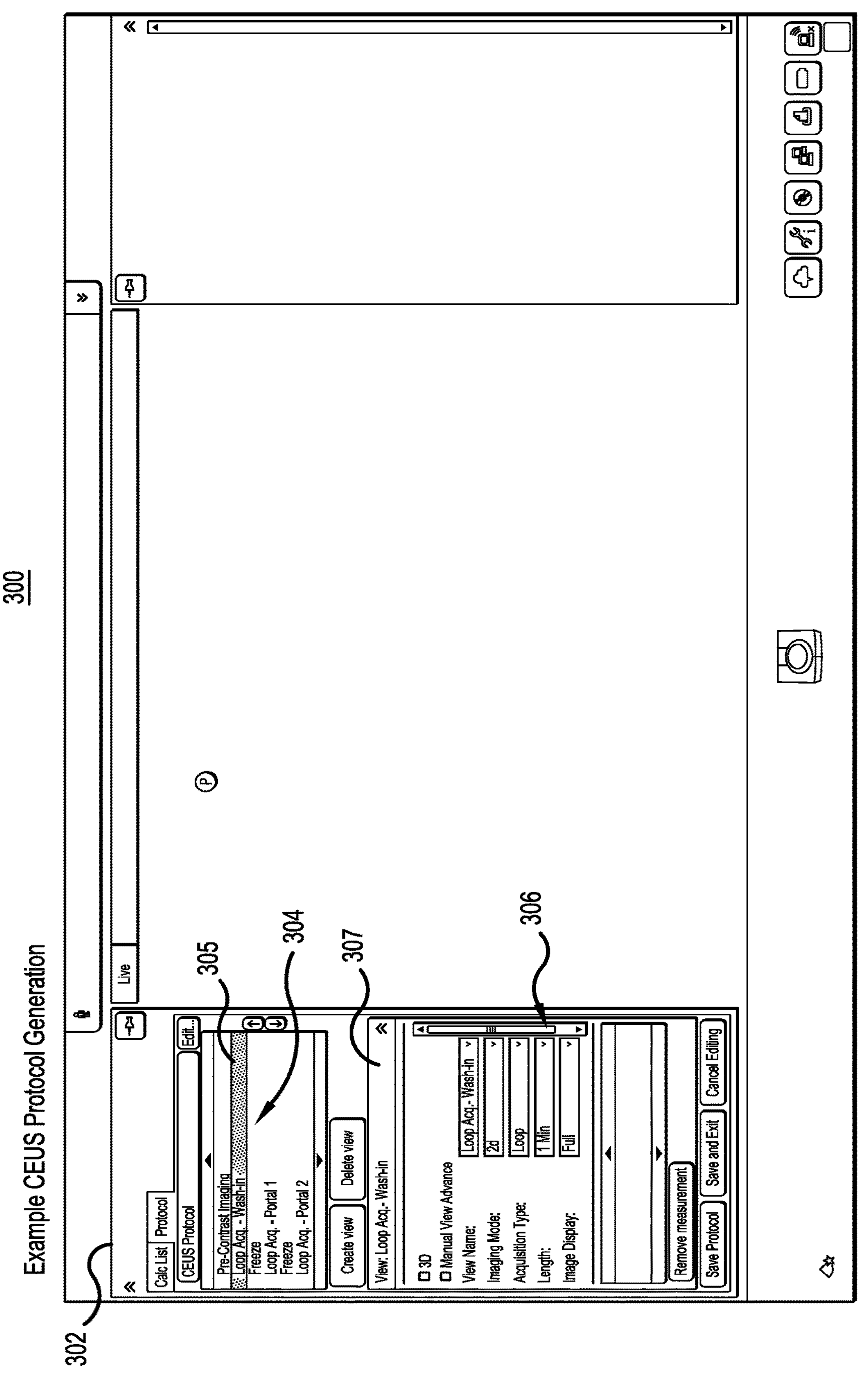
FIG. 3 is a view of a display comprising a menu for generating a CEUS protocol according to a representative embodiment.

FIG. 3 is a first time-bar display 300 shown on display 150 comprising a menu 302 for generating a CEUS protocol according to a representative embodiment. Various aspects and details of the first time-bar display 300 on the display 150 and menu 302 are common to those described above in connections with FIGS. 1 and 2, and may not be repeated in order to avoid obscuring the discussion of the present representative embodiment. Notably, the first time-bar display 300 is an example of a time-bar display adapted to alter time-based actions during the CEUS imaging exam, and to provide visual indications of upcoming actions on the display 150. As such, a number of the actions described in connection with FIG. 2 may be selected during the generation of the protocol using the menu 302 of the first time-bar display 300. These time-based actions include, but are not limited to, changes to ultrasound settings including one or more of a change in a number of ultrasonic signal transmissions, a pulse repetition interval between consecutive ultrasonic signal transmissions, a frequency of the ultrasonic signals, a specific type of ultrasonic pulse sequence. (e.g., Pulse Inversion and Amplitude Modulation), and a frame rate of captured ultrasonic images.

The menu 302 comprises a first sub-menu 304 and a second sub-menu 306. The first sub-menu 304 provides a plurality of options that are generally contrast-specific in nature. In generating the protocol, the user/operator selects options on a first drop-down menu 305. These options include those described above in connection with FIG. 2, including but are not limited to the selection of pre-contrast imaging, loop acquisition during wash-in, a first freeze, a first loop acquisition at portal phase, a second freeze, a second loop acquisition at portal phase, frame rate adjustment and gain. As alluded to above, the menu 302, the first sub-menu 304 and the first drop-down menu 305 are created by execution of instructions stored in memory 130 by the controller 120, and are modified using the user interface 160, or the GUI 155, or both. Illustratively, the first and second loop acquisition at portal phases represent two total imaging loops that cover the 'portal phase' of a liver CEUS exam, which is the period in which contrast agent arrives in the liver from the hepatic portal vein. For this example, several 30 second loop acquisitions may happen in the same phase, and the numbering is just the sequence followed (e.g., portal 1, portal 2, late 1, late 2 would represent two loop acquisitions in the portal phase, and two in the late phase).

A second drop-down menu 307 comprises options for timing of actions including but not limited start time, end time, and duration for the various actions described in connection with FIG. 2. Moreover, the second drop-down menu 307 may comprise options for altering a frame rate (number of transmits per frame) and/or transmit line density in order to preserve agent, depth, inclusion/exclusion of a side-by-side tissue reference, gain, dynamic range, as well as changing other acoustic properties of the acquisition relative to prior protocol events.

As alluded to above, the second sub-menu 306 and the second drop-down menu 307 are created by execution of instructions stored in memory 130 by the controller 120, and are modified using the user interface 160, or the GUI 155, or both.

Notably, the selection of an option from the first drop-down menu 305 causes the second drop down menu to provide various options for the selected action of the first drop-down menu 305. For example, the first time-bar display 300 shows the selection of "Loop Acquisition-Wash In" in the first drop-down menu 305. The selection of "Loop Acquisition-Wash In" on the first drop-down menu 305 causes the display of various options on the second drop-down menu 307 that are useful to the selected action of the protocol, which then provides options "Loop Acquisition-Wash In." These include the ability to select the imaging mode (3D or 2D), the type of acquisition (loop, image, or both), the duration of the selected action (in this case Loop Acquisition-Wash In), and the desired portion of the display 150 shown during this portion of the protocol. Other options available to the user in the second drop-down menu 307 include many described above including start and end times, and the ability to select alerts and prompts presented on the display 150 during execution of the particular protocol selected. Illustratively, and as described in connection with FIG. 4 below, these alerts and prompts are presented on the display so upcoming actions are readily accessible by the user/operator of the imaging system 100.

Figure 4:
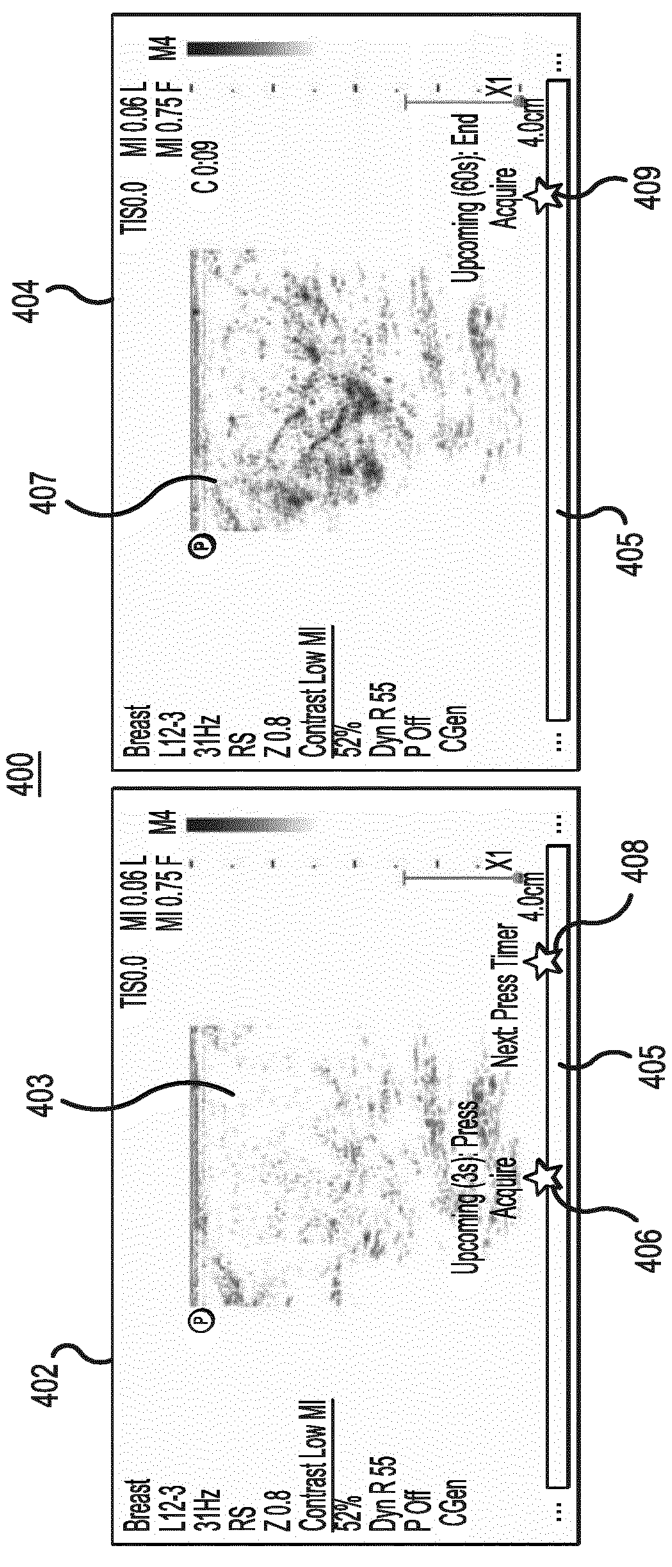
FIG. 4 is a view of a display during real-time acquisition of images according to a representative embodiment.

FIG. 4 is a second time-bar display 400 on the display on the display 150 during real-time acquisition of images according to a representative embodiment. Various aspects and details of the second time-bar display 400 on the display 150 are common to those described above in connections with FIGS. 1-3, and may not be repeated in order to avoid obscuring the discussion of the present representative embodiment. As alluded to above, the various alerts and prompts, their timing or duration, or both, presented in the second time-bar display 400 on the display 150 are selected by the user/operator during generation of the protocol (e.g., using first time-bar display 300 on the display on the display 150), and are created by execution of instructions stored in memory 130 by the controller 120, and are selected using the user interface 160, or the GUI 155, or both.

The second time-bar display 400 shows a first screen 402 and a second screen 404 with CEUS images 403 and 407, respectively. The first and second screens 402, 404 further comprise a bar 405 that scrolls based on event or action triggers and timing specifications for actions to be taken by the user operator. As shown in the first screen 402, a first alert 406 is provided to prompt the user/operator to be ready for an upcoming action in a specified time (e.g., 3 s) of the generated protocol. As noted above, in addition to the display of the first alert 406, an audio alert, or a haptic alert, or both may accompany the first alert 406. After the passing of the first alert 406, a first prompt 408 shows the appropriate time for the user/operator to engage the timer for the action being taken. In the present example, the first alert 406 and the first prompt 408 are used to ensure an image/loop acquisition is carried out beginning at a particular time during the imaging scan and according to the generated protocol.

As shown in the second screen 404, a second alert 409 is displayed to prompt the user/operator to terminate the image/loop acquisition at the time specified by the protocol (e.g., using first time-bar display 300 on the display 150), and after the selected duration specified by the protocol. As noted above, in addition to the display of the first alert 406, an audio alert, or a haptic alert, or both may accompany the second alert 409. The second alert 409 shows the appropriate time for the user/operator to terminate the scan according to the protocol. Notably another alert (not shown) may be provided to warn the user/operator that the termination time of the current acquisition is upcoming. In the present example, the second alert 409 is used to ensure an image/loop acquisition, and is terminated at a particular time during the imaging scan and according to the generated protocol.

Figure 5:
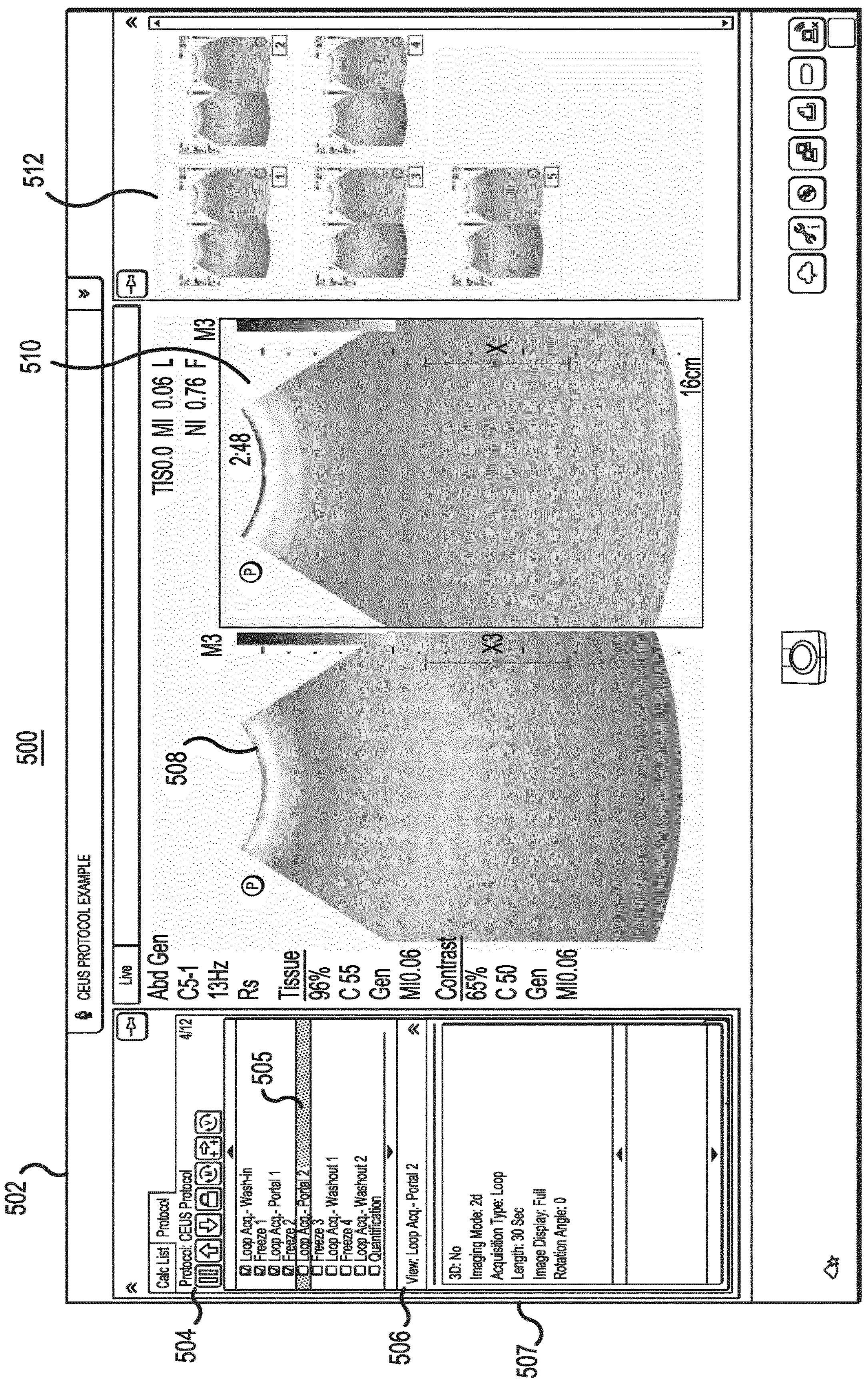
FIG. 5 is a view of a display showing various images/loops gathered during an imaging sequence according to a representative embodiment.

FIG. 5 is a view 500 on the display 150 comprising a menu 502 and showing various images/loops gathered during an imaging sequence according to a representative embodiment. Various aspects and details of the view 500 on the display 150 and menu 502 are common to those described above in connections with FIGS. 1-4, and may not be repeated in order to avoid obscuring the discussion of the present representative embodiment. Notably, the view 500 is an example of a second time-bar display 400 adapted to provide access to images/loops gathered during execution of a CEUS protocol generated using the first time-bar display 300 and the second time-bar display 400 described above. As such, a number of the actions described in connection with FIGS. 2-4 may be selected during the generation of the protocol using the menu 502 of the first time-bar display 300. Furthermore, view 500 is also contemplated for use both in a live imaging setting and a post-exam review.

The menu 502 comprises a first sub-menu 504 and a second sub-menu 506. As described more fully below, the first and second sub-menus 504, 506 allow a user/operator to review images gathered and transitions between actions taken during the various steps in the protocol generated as described in connection with FIGS. 2-3 above.

The first sub-menu 504 provides a list of the actions taken during the protocol the user/operator selected while generating the protocol. Options provided on a first drop-down menu 505 feature the actions. These options include those described above in connection with FIGS. 2 and 3, including, but are not limited to, the selection of images gathered in pre-contrast imaging, loop acquisitions during wash-in, a first freeze, a first loop acquisition at a portal phase, a second freeze, a second loop acquisition at another portal phase, a third freeze, loop acquisitions during a first wash-out, a fourth freeze, a third loop acquisition during a wash-out, and quantification. As alluded to above, the menu 502 and the first drop-down menu 505 are created by execution of instructions stored in memory 130 by the controller 120, and are modified using the user interface 160, or the GUI 155, or both.

The second drop-down menu 507 comprises a list the various parameters of the selected portion of the CEUS imaging scan of the generated protocol. The second drop-down menu 507 includes the various timing of actions including but not limited start time, end time, and duration for the various actions selected using second drop-down menu 307 described in connection with FIG. 3. As alluded to above, the second sub-menu 506 and the second drop-down menu 507 arc created by execution of instructions stored in memory 130 by the controller 120, and are modified using the user interface 160, or the GUI 155, or both. View 500 also shows selected images 508, 510 from a number of images 512 gathered during the selected portion of the protocol. Specifically, view 500 comprises a panel showing a number of images 512 gathered during the second loop acquisition selected from first drop-down menu 505.

View 500 shows the loops acquired in sequence during the entire protocol. Images 512 represent thumbnails from the loops taken in the previous steps through the current step. In an example, the review bar on the right hand side of view 500 could be set to display the images in a time sequence with appropriate labels (e.g. separate containing boxes for each phase, or in a line with timing denoted next to the thumbnails and annotations regarding which step in the protocol they were taken from). In a live imaging setting, the right hand elements in images 512 would represent the past events in the current and/or previous sequences and selected images 508, 510 would represent the live image at the current instance of scanning. In this context, the left hand side of view 500 represents past/present/upcoming events, and check marks indicate what has already been completed.

The user/operator can select images 508, 510 from the images 512 for further review after completion of the protocol. Notably, the images 512 include the time of their acquisition during the protocol, and therefore, allow the user/operator to select certain images for further review. Just by way of illustration, buttons can be used to add indications that these buttons can be used to move through the protocol. For example, in a live imaging mode, button 516 to the left of a trackball circle 514 could be used to repeat the previous protocol element, middle button 518 at the top of the trackball circle 514 could be used to advance to the next protocol element, and button 520 to the right of the trackball circle 514 could be used to end the exam and advance to review. If this display were used in review, the same button assignments could be used to move between loops/images taken at previous and next protocol elements.

Figure 6:
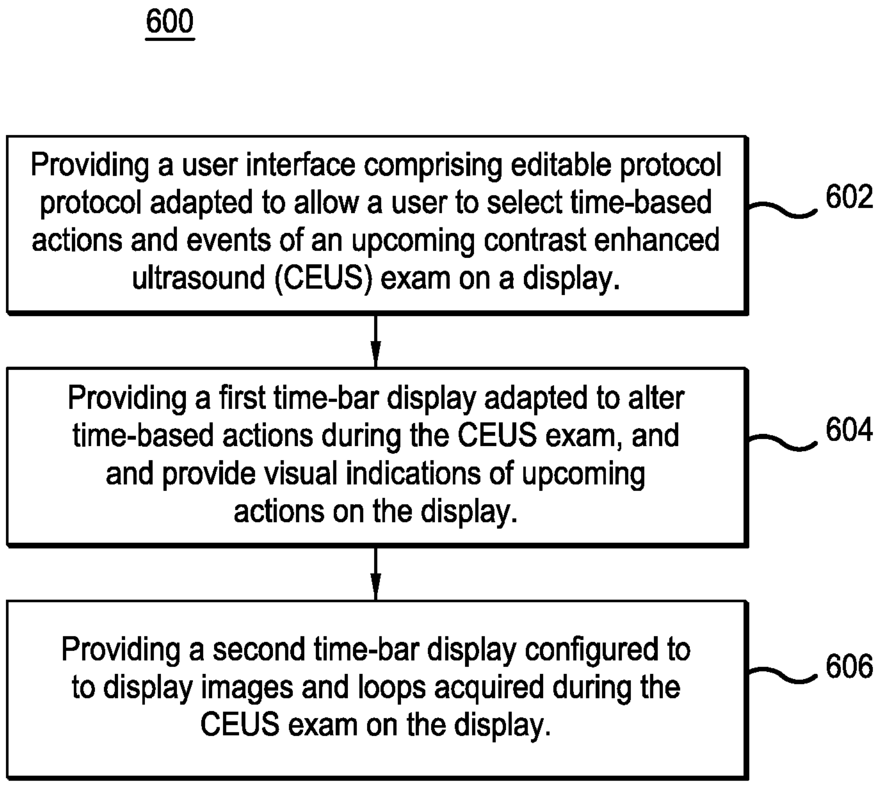
FIG. 6 is a flow diagram showing a method of imaging a portion of a subject, according to a representative embodiment.

FIG. 6 is a flow diagram showing a method 600 of imaging a portion of a subject, according to a representative embodiment. Various aspects of the method and details of the flow diagram and the attendant method 600 are common to those described above, and may not be repeated in order to avoid obscuring the discussion of the present representative embodiment. Most notably, the method 600 is contemplated for not only the method, but also for storing in a tangible, non-transitory computer readable medium that stores instructions, which when executed by a processor, cause the processor to carry out the method 600. Finally, while the method 600 is contemplated for use in CEUS imaging, the method 600 may be used in other systems to facilitate imaging protocol is using a menu on a display, a user interface and/or a GUI, real time reminders and alerts provided on a display, and image/loop review on the display.

At 602, the method begins by providing a user interface comprising editable protocol adapted to allow a user to select time-based actions and events of an upcoming contrast enhanced ultrasound (CEUS) exam on a display.

At 604 the method comprises providing a first time-bar display adapted to alter time-based actions during the CEUS exam, and provide visual indications of upcoming actions on the display.

At 606, the method comprises providing a second time-bar display configured to display images and loops acquired during the CEUS exam on the display.

As will be appreciated by one of ordinary skill in the art having the benefit of the present disclosure, the systems and methods of the present teachings provide an improvement in the implementation of imaging protocols, such as used in CEUS imaging. For example, compared to known methods and systems, various aspects of a protocol including the beginning, duration and termination of a step in the protocol can be facilitated during the generation of the protocol, or during implementation of the protocol, or both. Moreover, errors that can result from human interaction with an imaging system can be reduced thereby reducing the need to repeat procedures, and reducing the time required to complete an imaging procedure. Notably, these benefits are illustrative, and other advancements in the field of medical imaging will become apparent to one of ordinary skill in the art having the benefit of the present disclosure.

Although methods, systems and components for implementing imaging protocols have been described with reference to several exemplary embodiments, it is understood that the words that have been used are words of description and illustration, rather than words of limitation. Changes may be made within the purview of the appended claims, as presently stated and as amended, without departing from the scope and spirit of the protocol implementation of the present teachings.

The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents and shall not be restricted or limited by the foregoing detailed description.

The invention claimed is:

1. A display for a contrast-enhanced ultrasound (CEUS) exam, the display comprising:

a monitor;

a menu comprising selectable components of an editable protocol adapted to allow a user to select time-based actions and events of an upcoming CEUS exam on the display, wherein the selected time-based actions and events are shown during the CEUS exam on a scrolling time bar;

a first time-bar display adapted to allow the user to alter time-based actions during the CEUS exam, and to provide visual indications of upcoming actions on the display; and a second time-bar display adapted to allow the user to display images and loops acquired during the CEUS exam on the display.

2. The display of claim 1, wherein the time-based actions comprise image or loop acquisitions, or both.

3. The display of claim 1, wherein the selected time-based actions comprise changes to ultrasound settings comprising one or more of: a change in a number of ultrasonic signal transmissions; a pulse repetition interval between consecutive ultrasonic signal transmissions; a frequency of the ultrasonic signals; an ultrasonic pulse sequence; and a frame rate of captured ultrasonic images.

4. The display of claim 3, wherein the time-based actions comprise changes to acoustic settings to adjust one or more of a number of acoustic signal transmissions, an acoustic signal frequency, and a frame rate of acquisitions.

5. The display of claim 1, wherein the time-based actions comprise ultrasound freeze and unfreeze actions.

6. The display of claim 1, wherein the selected time-based actions and events are enhanced by audio or haptic prompts.

7. The display of claim 1, wherein the second time-bar display is adapted to link a particular point in the editable protocol with an image or a loop acquired during the CEUS exam.

8. A system for medical imaging, comprising the display of claim 1.

9. The display of claim 1, wherein during scheduling of the editable protocol, the user selects an alert on the monitor, the alert denoting a specified time when an operator must take action during the CEUS exam.

10. The display of claim 9, wherein the alert comprises at least one of a visual alert on the monitor, an audio alert, and a haptic alert.

11. A method of controlling an imaging procedure, the method comprising:

providing a menu comprising editable protocol adapted to allow a user to select time-based actions and events of an upcoming contrast enhanced ultrasound (CEUS) exam on a display;

providing a first time-bar display adapted to alter time-based actions during the CEUS exam, and provide visual indications of upcoming actions on the display;

providing a second time-bar display configured to display images and loops acquired during the CEUS exam on the display; and displaying the selected time-based actions and events during the CEUS exam on a scrolling time bar.

12. The method of claim 11, wherein the time-based actions comprise ultrasound freeze and unfreeze controls.

13. The method of claim 11, wherein the selected time-based actions and events are enhanced by audio or haptic prompts.

14. The method of claim 11, wherein the second time-bar display is adapted to link a particular point in the editable protocol with an image or a loop acquired during the CEUS exam.

15. The method of claim 11, wherein the second time-bar display is adapted to provide images or loops at particular times of the CEUS exam by navigating across the second time-bar display.

16. The method of claim 11, wherein the user interface comprising a graphic user interface (GUI) adapted to function with the display.

17. The method of claim 11, further comprising, during scheduling, selecting an alert on a monitor, which denotes a specified time when an operator must take action during the CEUS exam.

18. The method of claim 17, wherein the alert comprises at least one of a visual alert on the monitor, an audio alert, and a haptic alert.

19. A tangible, non-transitory computer-readable medium that stores instructions, which when executed by a processor, cause the processor to:

provide a menu comprising editable protocol adapted to allow a user to select time-based actions and events of an upcoming contrast enhanced ultrasound (CEUS) exam on a display, wherein the selected time-based actions and events are shown during the CEUS exam on a scrolling time bar;

provide a first time-bar display adapted to alter time-based actions during the CEUS exam, and provide visual indications of upcoming actions on the display; and provide a second time-bar display configured to display images and loops acquired during the CEUS exam on the display.

20. The tangible, non-transitory computer-readable medium of claim 19, wherein the time-based actions comprise image or loop acquisitions, or both.

21. The tangible, non-transitory computer-readable medium of claim 19, wherein the time-based actions comprise ultrasound freeze and unfreeze controls.

22. The tangible, non-transitory computer-readable medium of claim 19, wherein the selected time-based actions and events are enhanced by audio or haptic prompts.

23. The tangible, non-transitory computer-readable medium of claim 19, wherein the second time-bar display is adapted to link a particular point in the editable protocol with an image or a loop acquired during the CEUS exam.

24. The tangible, non-transitory computer-readable medium of claim 17, wherein the second time-bar display is adapted to provide images or loops at particular times of the CEUS exam by navigating across the second time-bar display.

25. The tangible, non-transitory computer-readable medium of claim 19, wherein during scheduling of the editable protocol, the user selects an alert on a monitor, the alert denoting a specified time when an operator must take action during the CEUS exam.

26. The tangible, non-transitory computer-readable medium of claim 25, wherein the alert comprises at least one of a visual alert on the monitor, an audio alert, and a haptic alert.

* * * * *